(12) United States Patent
Kang et al.

(10) Patent No.: US 11,408,886 B2
(45) Date of Patent: Aug. 9, 2022

(54) METHOD OF SCREENING FOR NOVEL THERAPEUTIC TARGETS TO DEVELOP THERAPEUTIC AGENTS FOR COLON CANCER AND PROGNOSTIC BIOMARKERS FOR COLON CANCER TREATMENT SCREENED USING THE SAME

(71) Applicant: KOREA INSTITUTE OF SCIENCE AND TECHNOLOGY, Seoul (KR)

(72) Inventors: Min-Jung Kang, Seoul (KR); Byung Hwa Jung, Seoul (KR); Young Sook Yoo, Seoul (KR); Thanh Binh Nguyen, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 606 days.

(21) Appl. No.: 16/427,655

(22) Filed: May 31, 2019

(65) Prior Publication Data
US 2019/0369101 A1 Dec. 5, 2019

(30) Foreign Application Priority Data

May 31, 2018 (KR) .......................... 10-2018-0062865

(51) Int. Cl.
*G01N 31/00* (2006.01)
*G01N 33/53* (2006.01)
*G01N 33/574* (2006.01)
*G16B 35/20* (2019.01)
*G01N 33/50* (2006.01)
*C12N 5/071* (2010.01)

(52) U.S. Cl.
CPC ..... *G01N 33/57419* (2013.01); *C12N 5/0679* (2013.01); *G01N 33/5011* (2013.01); *G16B 35/20* (2019.02); *G01N 2560/00* (2013.01)

(58) Field of Classification Search
None
See application file for complete search history.

(56) References Cited

FOREIGN PATENT DOCUMENTS

| KR | 10-2005-0052663 A | 6/2005 |
| KR | 10-0934706 B1 | 12/2009 |
| KR | 10-1691536 B1 | 1/2017 |

OTHER PUBLICATIONS

Itoh et al. (Cytoskeleton, May 2010 67:297-308) (Year: 2010).*
Monika Raab et al., "PLK1 has tumor-suppressive potential in APC truncated colon cancer cells", Nature Communications, Mar. 16, 2018, pp. 1-17.

* cited by examiner

*Primary Examiner* — Lisa V Cook
(74) *Attorney, Agent, or Firm* — Cantor Colburn LLP

(57) ABSTRACT

Provided are a method of screening for novel therapeutic targets to develop therapeutic agents for colon cancer, and prognostic biomarkers for colon cancer treatment which are screened using the same.

18 Claims, 18 Drawing Sheets

FIG. 9A

| IDs | Description | Score |
|---|---|---|
| ABL1 | Tyrosine-protein kinase ABL1 | 60 |
| ABL2 | Abelson tyrosine-protein kinase 2 | 32 |
| ACTB | Actin, cytoplasmic 1 | 42 |
| ACTN4 | Actinin, alpha 4 | 31 |
| ARHGEF1OL | Rho guanine nucleotide exchange factor 25 | 33 |
| B4GN3 | Beta-1,4-N-acetylgalactosaminyltransferase 3 | 43 |
| CADH6 | Cadherin-6 | 26 |
| CATL2 | Cathepsin L2 | 27 |
| CC125 | Coiled-coil domain-containing protein 125 | 29 |
| CC160 | Coiled-coil domain-containing protein 160 | 30 |
| CCDC146 | Coiled-coil domain-containing 146 | 28 |
| CDK13 | Cyclin-dependent kinase 13 | 36 |
| CDKL3 | Cyclin-dependent kinase-like 3 | 37 |
| CLSPN | Claspin | 29 |
| COGA1 | Collagen alpha-1(XVI) chain | 35 |
| CXD4 | Gap junction delta-4 protein | 27 |
| CYS1 | Cystin-1 | 30 |
| DESP | Desmoplakin | 33 |
| DJB11 | DnaJ homolog subfamily B member 11 | 35 |
| DMBT1 | Deleted in malignant brain tumors 1 protein | 29 |
| DSP | Desmoplakin | 27 |
| DYH9 | Dynein heavy chain 9, axonemal | 29 |
| ELAVL1 | ELAV like RNA binding protein 1 | 30 |
| ELAVL4 | ELAV like RNA binding protein 4 | 29 |
| EPB41L4A | erythrocyte membrane protein band 4.1 like 4A | 27 |
| FAK1 | Focal adhesion kinase 1 | 460 |
| FAK2 | Protein-tyrosine kinase 2-beta | 35 |
| FLN | Filamin | 45 |
| GFAP | Glial fibrillary acidic protein | 75 |
| GRB14 | Growth factor receptor-bound protein 14 | 33 |
| GSL3A | Glycogen synthase kinase-3 alpha | 36 |
| GTPB1 | GTP-binding protein 1 | 27 |
| HORN | Hornerin | 47 |
| HSP7C | Heat shock cognate 71 kDa protein | 27 |
| ILK | Integrin-linked protein kinase | 29 |
| INT12 | Integrator complex subunit 12 | 27 |
| IQGA2 | Ras GTPase-activating-like protein IQGAP2 | 31 |
| KLHL8 | Kelch like family member 8 | 28 |
| KLK6 | Kallikrein-6 | 30 |
| KRIT1 | Krev interaction trapped protein 1 | 30 |
| LACRT | Extracellular glycoprotein lacritin | 34 |
| LATS1 | Serine/threonine-protein kinase LATS1 | 39 |
| LIRB4 | Leukocyte immunoglobulin-like receptor subfamily B member 4 | 25 |
| LMOD3 | Leiomodin-3 | 26 |
| LRRC4 | Leucine-rich repeat-containing protein 4 | 30 |

FIG. 9B

| IDs | Description | Score |
|---|---|---|
| MA7D2 | MAP7 domain-containing protein 2 | 33 |
| MP2K3 | Dual specificity mitogen-activated protein kinase kinase 3 | 35 |
| MP2K4 | Dual specificity mitogen-activated protein kinase kinase 4 | 28 |
| MYH7B | Myosin heavy chain 7B | 26 |
| MYO3G | Myosin-IIIa | 36 |
| MYO5A | Unconventional myosin-Va | 28 |
| MYO1D | Myosin 1D | 30 |
| NMDE1 | Glutamate receptor ionotropic, NMDA 2A | 27 |
| NOC4L | Nucleolar complex protein 4 homolog | 26 |
| PI4KA | Phosphatidylinositol 4-kinase alpha | 26 |
| PI4KB | Phosphatidylinositol 4-kinase beta | 28 |
| PLK1 | Serine/threonine-protein kinase PLK1 | 35 |
| PLXA1 | Plexin-A1 | 28 |
| PLXA2 | Plexin-A2 | 25 |
| PPP1R12B | Protein phosphatase 1 regulatory subunit 12B | 27 |
| PTN | Pleiotrophin | 30 |
| RB22A | Ras-related protein Rab-22A | 30 |
| RCC1 | Regulator of chromosome condensation | 27 |
| RHG01 | Rho GTPase-activating protein 1 | 28 |
| RHG07 | Rho GTPase-activating protein 7 | 27 |
| RHG28 | Rho GTPase-activating protein 28 | 26 |
| RHOU | Rho-related GTP-binding protein RhoU | 27 |
| RPC1 | DNA-directed RNA polymerase III subunit RPC1 | 26 |
| SACS | Sacsin | 35 |
| SHPRH | E3 ubiquitin-protein ligase SHPRH | 29 |
| SMAD6 | Mothers against decapentaplegic homolog 6 | 31 |
| SPTN5 | Spectrin beta chain, non-erythrocytic 5 | 26 |
| SRCN1 | SRC kinase signaling inhibitor 1 | 29 |
| STA13 | StAR-related lipid transfer protein 13 | 30 |
| STAR9 | StAR-related lipid transfer protein 9 | 30 |
| SYNE1 | Nesprin-1 | 33 |
| SYNE3 | Nesprin-3 | 32 |
| TJP1 | Tight junction protein ZO-1 | 41 |
| TJP3 | Isoform 3 of Tight junction protein ZO-3 | 39 |
| TGFI1 | Transforming growth factor beta-1-induced transcript 1 protein | 28 |
| VGFR1 | Vascular endothelial growth factor receptor 1 | 30 |
| YK022 | Putative uncharacterized protein FLJ42102 | 32 |
| ZN408 | Zinc finger protein 408 | 33 |
| ZN503 | Zinc finger protein 503 | 30 |
| ZXDC | Zinc finger protein ZXDC | 31 |
| ZYX | Zyxin | 46 |

FIG. 10

| IDs | Description | Disease |
|---|---|---|
| ABL1 | Tyrosine-protein kinase ABL1 OS=Homo sapiens GN=ABL1 PE=1 SV=4 | Cancer (Leukemia) |
| ELAVL1 | ELAV like RNA binding protein 1 OS=Homo sapiens GN=ELAVL1 PE=1 SV=1 | Cancer (Breast, Colon) |
| GRB14 | Growth factor receptor-bound protein 14 OS=Homo sapiens GN=GRB14 PE=1 SV=2 | Cancer (Colon) |
| GSK3A | Glycogen synthase kinase-3 alpha OS=Homo sapiens GN=GSK3A PE=1 SV=2 | Cancer (Breast, Lung, Prostate) |
| HORN | Hornerin OS=Homo sapiens GN=HRNR PE=1 SV=2 | Cancer (Breast) |
| LATS1 | Serine/threonine-protein kinase LATS1 OS=Homo sapiens GN=LATS1 PE=1 SV=1 | Cancer (Kidney) |
| LRRC4 | Leucine-rich repeat-containing protein 4 OS=Homo sapiens GN=LRRC4 PE=1 SV=2 | Not Specified |
| MA7D2 | MAP7 domain-containing protein 2 OS=Homo sapiens GN=MAP7D2 PE=1 SV=2 | Cancer (Colon) |
| MP2K3 | Dual specificity mitogen-activated protein kinase kinase 3 OS=Homo sapiens GN=MAP2K3 PE=1 SV=2 | Cancer (Ovarian) |
| MP2K4 | Dual specificity mitogen-activated protein kinase kinase 4 OS=Homo sapiens GN=MAP2K4 PE=1 SV=1 | Cancer (Ovarian) |
| PI4KA | Phosphatidylinositol 4-kinase alpha OS=Homo sapiens GN=PI4KA PE=1 SV=3 | Cancer (Breast) |
| PI4KB | Phosphatidylinositol 4-kinase beta OS=Homo sapiens GN=PI4KB PE=1 SV=1 | Cancer (Breast) |
| PLK1 | Serine/threonine-protein kinase PLK1 OS=Homo sapiens GN=PLK1 PE=1 SV=1 | Cancer (Colon) |
| SHPRH | E3 ubiquitin-protein ligase SHPRH OS=Homo sapiens GN=SHPRH PE=1 SV=2 | Not specified |
| SYNE1 | Nesprin-1 OS=Homo sapiens GN=SYNE1 PE=1 SV=4 | Cancer (Epithelial type) |
| SYNE3 | Nesprin-3 OS=Homo sapiens GN=SYNE3 PE=1 SV=2 | Cancer (Epithelial type) |
| VGFR1 | Vascular endothelial growth factor receptor 1 OS=Homo sapiens GN=FLT1 PE=1 SV=2 | Cancer (Kidney) |
| ZYX | Zyxin OS=Homo sapiens GN=ZYX PE=1 SV=1 | Cancer (Leukemia) |

FIG. 11
(a) LOCATION OF PROTEIN EXPRESSION
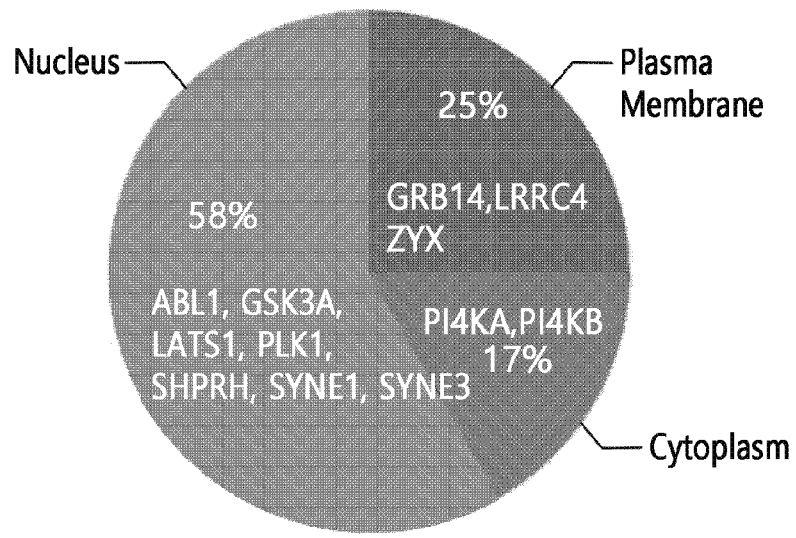
(b) KINDS OF PROTEINS
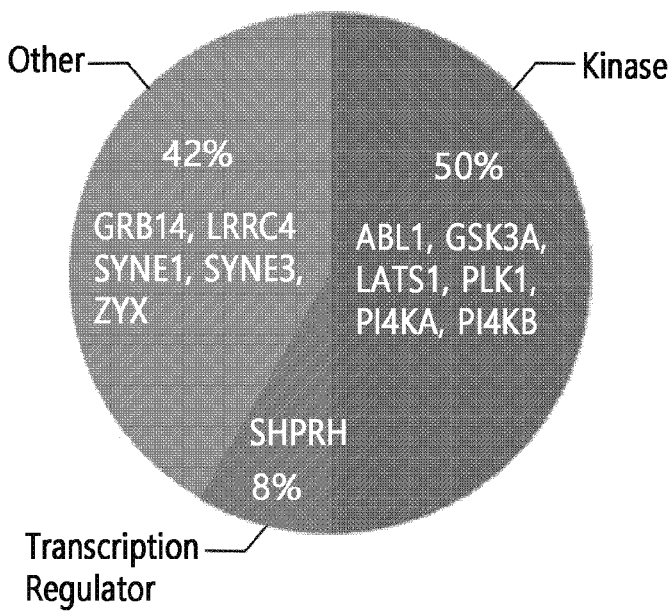

FIG. 13A

|    | Description | Gene symbol | Treatment/Control |
|----|---|---|---|
| 1  | Kelch-like protein 8 [OS=Homo sapiens] | KLHL8 | 36.4 |
| 2  | Filamin [OS=Homo sapiens] | FLN | 22.8 |
| 3  | Isoform 9 of Nesprin-1 [OS=Homo sapiens] | SYNE1 | 19.7 |
| 4  | band 4.1-like protein 4A [OS=Homo sapiens] | EPB41L4A | 23.7 |
| 5  | Protein phosphatase 1 regulatory subunit 12b [OS=Homo sapiens] | PPP1R12B | 33.4 |
| 6  | Isoform 3 of Nesprin-1 [OS=Homo sapiens] | SYNE1 | 34.9 |
| 7  | Myosin-7B [OS=Homo sapiens] | MYH7B | 45.2 |
| 8  | Unconventional myosin-Id [OS=Homo sapiens] | MYO1D | 27.8 |
| 9  | Isoform 11 of Nesprin-1 [OS=Homo sapiens] | SYNE1 | 32.1 |
| 10 | Isoform 8 of Nesprin-1 [OS=Homo sapiens] | SYNE2 | 48.3 |
| 11 | Isoform 2 of Nesprin-1 [OS=Homo sapiens] | SYNE1 | 39.5 |
| 12 | Isoform 4 of Nesprin-1 [OS=Homo sapiens] | SYNE1 | 45.0 |
| 13 | Nesprin-1 [OS=Homo sapiens] | SYNE1 | 67.6 |
| 14 | Tight junction protein ZO-1 [OS=Homo sapiens] | TJP1 | 18.3 |
| 15 | Claspin [OS=Homo sapiens] | CLSPN | 26.9 |
| 16 | Coiled-coil domain-containing protein 146 [OS=Homo sapiens] | CCDC146 | 36.8 |
| 17 | Alpha-actinin-4 [OS=Homo sapiens] | ACTN4 | 65.5 |
| 18 | Focal adhesion kinase 1 [OS=Homo sapiens] | PTK2 | 20.6 |

FIG. 13B

|  | Description | Gene symbol | Treatment/Control |
|---|---|---|---|
| 1 | CD99 antigen [OS=Homo sapiens] | CD99 | 29.2 |
| 2 | Transmembrane emp24 domain-containing protein 2 [OS=Homo sapiens] | TMED2 | 36.5 |
| 3 | Isoform 3 of ELAV-like protein 4 [OS=Homo sapiens] | ELAVL4 | 56.4 |
| 4 | Isoform 3 of Serine/threonine-protein kinase PAK 3 [OS=Homo sapiens] | PAK3 | 19.8 |
| 5 | Platelet-derived growth factor subunit B [OS=Homo sapiens] | PDGFB | 34.4 |
| 6 | Unconventional myosin-Id [OS=Homo sapiens] | MYO1D | 24.6 |
| 7 | Clathrin heavy chain 1 [OS=Homo sapiens] | CLTC | 17.5 |
| 8 | Catenin alpha-2 [OS=Homo sapiens] | CTNNA2 | 16.9 |
| 9 | Isoform 8 of Filamin-B [OS=Homo sapiens] | FLNB | 42.3 |
| 10 | Tight junction protein ZO-1 [OS=Homo sapiens] | TJP1 | 14.7 |
| 11 | Puratrophin-1 [OS=Homo sapiens] | PLEKHG4 | 39.8 |
| 12 | Isoform 3 of Tight junction protein ZO-3 [OS=Homo sapiens] | TJP3 | 20.6 |
| 13 | Isoform 5 of Focal adhesion kinase 1 [OS=Homo sapiens] | PTK2 | 36.4 |
| 14 | Isoform 2 of Eukaryotic translation initiation factor 5A-1 [OS=Homo sapiens] | EIF5A | 16.8 |

FIG. 13C

| | Description | Gene symbol | Treatment/Control |
|---|---|---|---|
| 1 | Rho guanine nucleotide exchange factor 10-like protein [OS=Homo sapiens] | ARHGEF10L | 29.2 |
| 2 | Isoform 6 of Tight junction protein ZO-3 [OS=Homo sapiens] | TJP3 | 36.5 |
| 3 | Isoform DPII of Desmoplakin [OS=Homo sapiens] | DSP | 56.4 |
| 4 | Isoform 2 of Rho guanine nucleotide exchange factor 10-like protein [OS=Homo sapiens] | ARHGEF10L | 19.8 |
| 5 | Isoform 5 of Rho guanine nucleotide exchange factor 10-like protein [OS=Homo sapiens] | ARHGEF10L | 34.4 |
| 6 | Isoform 4 of Tight junction protein ZO-3 [OS=Homo sapiens] | TJP3 | 24.6 |
| 7 | Tight junction protein ZO-3 [OS=Homo sapiens] | TJP3 | 17.5 |
| 8 | Desmoplakin [OS=Homo sapiens] | DSP | 16.9 |
| 9 | Hepatocyte growth factor receptor [OS=Homo sapiens] | MET | 42.3 |

FIG. 13D

| | Description | Gene symbol | Treatment/Control |
|---|---|---|---|
| 1 | Unconventional myosin-Id [OS=Homo sapiens] | MYO1D | 19.7 |
| 2 | Isoform DPII of Desmoplakin [OS=Homo sapiens] | DSP | 26.4 |
| 3 | Isoform 4 of Inhibitor of nuclear factor kappa-B kinase-interacting protein [OS=Homo sapiens] | IKBIP | 35.9 |
| 4 | Desmoplakin [OS=Homo sapiens] | DSP | 44.6 |
| 5 | Isoform 5 of Focal adhesion kinase [OS=Homo sapiens] | PTK2 | 17.1 |

FIG. 14

| | VS 0.1 mM | VS 1 mM | VS 10 mM | PF 0.1 mM | PF 1 mM | PF 10 mM | Combined 0.1 mM | Combined 1 mM | Combined 10 mM |
|---|---|---|---|---|---|---|---|---|---|
| ZYX | 9.01 | 1.23 | 0 | 3.32 | 0.17 | 0.16 | 0 | 0 | 0 |
| ELAVL1 | 1.70 | 0.61 | 0.41 | No change | No change | No change | No change | No change | 0.74 |
| SYNE1 | 0 | 0 | 0 | 0.12 | 0 | 0 | 0 | 0 | 0 |
| RAB | 0.71 | 1.14 | No change | 0.37 | 0.52 | 0.28 | 1.16 | 0.64 | 0 |
| CAPN | No change | No change | 0 | 0.68 | 0.65 | 0.79 | 0.54 | 1.11 | 0 |
| MAP2K2 | 1.86 | 0.58 | 0 | No change | No change | No change | 0.73 | 0 | 0 |
| PPP2 | 0.54 | 0 | 0 | No change | No change | No change | 0 | 0 | 0 |
| ARFGEF | No change | No change | No change | 0 | 0 | 0 | 0 | 0 | 0 |

METHOD OF SCREENING FOR NOVEL THERAPEUTIC TARGETS TO DEVELOP THERAPEUTIC AGENTS FOR COLON CANCER AND PROGNOSTIC BIOMARKERS FOR COLON CANCER TREATMENT SCREENED USING THE SAME

BACKGROUND OF THE INVENTION

1. Field of the Invention

The present invention relates to a method of screening for novel therapeutic targets to develop therapeutic agents for colon cancer, and prognostic biomarkers for colon cancer treatment which are screened using the same.

2. Description of the Related Art

Colon cancer is the third most common cancer in Korea and the fourth leading cause of cancer-related deaths. It occurs more frequently in men than in women. Colon cancer is a disease that frequently occurs in Westerners who consume large amounts of fat or meat, and as the dietary patterns of Koreans become more westernized, its incidence is steadily increasing in Korea. In addition, colon cancer is not only difficult to detect because it has no subjective symptoms during the initial stage of the disease, but also, it has a poor prognosis and frequent metastasis after surgery. Therefore, it is necessary to develop biomarkers for prognosis as well as for diagnosis.

Currently used diagnostic methods for colon cancer include digital rectal examination, a carcinoembryonic antigen (CEA) test, a fecal occult blood test, colonography by double contrast Barium-enema, colonoscopy, computerized tomography (CT), CT colonography (virtual colonoscopy), magnetic resonance imaging (MRI), positron emission tomography-computerized tomography (PET-CT), etc., and specific biomarkers for diagnosis of colon cancer have not yet been identified.

The most frequently used therapeutic agent for colon cancer is the angiogenesis inhibitor Avastin, which creates a market worth around 1 trillion KRW annually. Angiogenesis inhibitors exhibit an anticancer effect by blocking nutritional supply to cancer cells, and are currently the most actively developed substances for use as a therapeutic agent for colon cancer. Among Korean companies, Bukwang Pharmaceutical Co., Ltd., Green Cross Corp., Samyang Genex Co., Ltd., Ilyang Pharm, Chong Kun Dang, Kolon, Donghwa Pharm, and JW Pharm Corp. are working on the development of angiogenesis inhibitors.

Meanwhile, the development of anticancer agents has focused on the combination of a targeted therapeutic agent and an immunotherapeutic agent, and immunotherapeutic agents such as vaccines, antibodies, etc. have been actively developed. Among these, the field of targeted therapeutic agents has seen development toward inhibitors (checkpoint inhibitors) capable of inhibiting binding of signaling substances to signaling receptors, angiogenesis inhibitors, and protein-protein interaction inhibitors. Development of the protein-protein interaction inhibitors as anticancer agent candidates has recently accelerated, as these are expected to have fewer side effects, unlike anti-cancer agents targeting the ATP binding site.

Furthermore, due to the nature of anticancer agents that have drug resistance and thus must be replaced with other therapeutic agents, it is necessary to identify novel target points of drugs for the development of targeted therapeutic agents of inhibiting protein-protein interactions with relatively few side effects.

PRIOR ART DOCUMENTS

Patent Documents

1) Korean Patent No. 10-0934706
2) Korean Patent Publication No. 10-2005-0052663
3) Korean Patent No. 10-1691536

Non-Patent Documents

1) Nature Communications (2018) DOI: 10.1038/s41467-018-03494-4. PLK1 has tumor-suppressive potential in APC truncated colon cancer cells. Monika Raab et al.

SUMMARY OF THE INVENTION

The present inventors have conducted intensive studies to develop a method of screening for target points of drugs for the development of targeted therapeutic agents that inhibit protein-protein interactions among proteins specifically binding to proteins overexpressed in cells of a colon cancer patient, as compared with intestinal epidermal cells of a normal person, and as a result, they found that novel target candidates for the development of colon cancer-specific targeted therapeutic agents may be screened by a series of processes including selection by immunoprecipitation, isolation by liquid chromatography-mass spectrometry, and identification using a proteomics database search engine, thereby completing the present invention.

BRIEF DESCRIPTION OF THE DRAWINGS

FIGS. 9A and 9B show the result of identifying proteins which were reproducibly detected three times or more among proteins specifically binding to FAK protein isolated from colon cancer cell samples, the proteins obtained by analyzing the IP results using a Mascot search engine, wherein a total of 84 proteins were identified and arranged in alphabetical order;

FIG. 10 shows total 18 kinds of binding proteins which are associated with cancer and expressed with higher frequency in cancer cells than in normal intestinal epidermal cells, the proteins obtained through a literature search;

FIG. 11 shows information on the in silico gene pathway of 12 kinds of proteins having networks with the FAK signaling pathway among the 18 kinds of the FAK-binding proteins shown in FIG. 10, wherein FIG. 11A shows the intracellular expression sites of the 12 kinds of the proteins, and FIG. 11B shows the results of categorizing the 12 kinds of the new drug target candidates into protein types;

FIGS. 13A to 13D show lists of proteins of which expression was increased 10 times or more in a colon cancer cell line HCT-116 treated with hEGF, hIGF-1, PDGF, and PMA, which are known to increase FAK signaling, as compared with cells not treated with the FAK signaling substance, wherein the FAK-binding proteins were obtained by analysis of nano-liquid chromatography/high-resolution mass spectrometry after in-gel digestion of Western blotting results and by identifying using a Mascot search engine; and FIG. 14 shows protein candidates showing significant changes in the expression levels, among proteins of colon cancer cells, when they were treated with the known FAK inhibitors, defactinib (VS-6063) and PF-573228, singly or in combination.

DETAILED DESCRIPTION OF THE PREFERRED EMBODIMENTS

Figure 1:
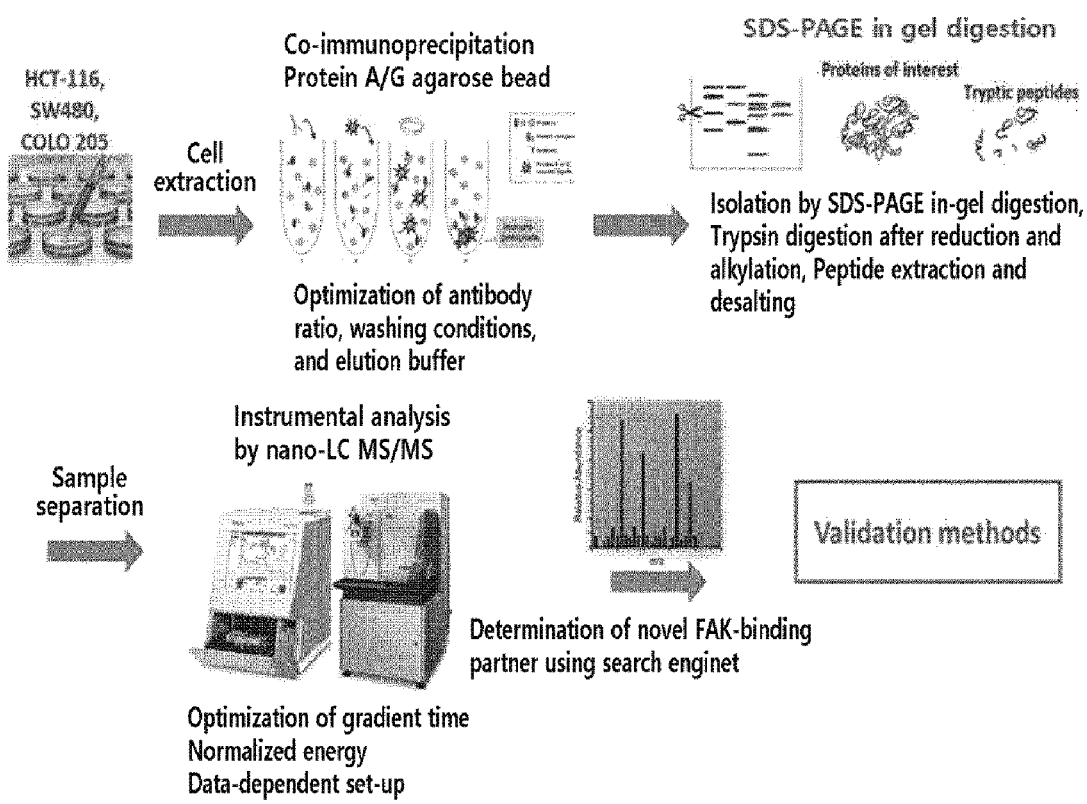
FIG. 1 is a schematic illustration of a method of screening for a novel target point for the development of an anticancer agent specifically targeting colon cancer according to the present invention.

A first aspect of the present invention provides a method of screening for therapeutic targets to develop therapeutic agents for colon cancer, the method including a first step of collecting proteins specifically binding to focal adhesion kinase (FAK), which is overexpressed in cells separated from a colon cancer patient, as compared with normal intestinal epidermal cells, by immunoprecipitation (IP) of a cell lysate of a colon cancer cell line or a cell separated from a colon cancer patient with an antibody against FAK which is overexpressed in cells separated from a colon cancer patient, as compared with normal intestinal epidermal cells; a second step of isolating and analyzing the proteins obtained from the first step by liquid chromatography-mass spectrometry; and a third step of identifying the proteins isolated and analyzed by the second step using a proteomics database search engine.

In a specific embodiment of the present invention, when FAK expression in a colon cancer cell line was measured and compared with FAK expression in stomach cancer, breast cancer, and lung cancer cell lines, remarkably increased FAK expression was observed in the colon cancer cell line, as compared with other cancer cell lines, and as a result, it was confirmed that FAK may be used as a target protein for the development of colon cancer-specific therapeutic agents.

The cell lysate may be a lysate of a colon cancer cell line cultured in a medium containing FAK signaling substances or a cell separated from a colon cancer patient. The FAK signaling substances may include phorbol 12-myristate 13-acetate (PMA), human epidermal growth factor (hEGF), human platelet-derived growth factor (PDGF), human insulin-like growth factor-1 (hIGF-1), or a combination thereof, but are not limited thereto. FAK signaling substances known in the art may be used alone or in combination without limitation. In a specific embodiment of the present invention, it was confirmed that the amount of FAK was increased two-fold or more in the lysates of cells treated with the four kinds of the FAK signaling substances.

For example, the immunoprecipitation may be performed using protein A/G agarose beads onto which FAK antibodies are immobilized, but is not limited thereto. In a specific embodiment of the present invention, it was confirmed that use of agarose beads as an immobilizer shows more excellent FAK adhesion than use of magnetic beads.

For example, in the immunoprecipitation, the step of removing nonspecifically bound proteins may be further performed by washing with a buffer containing 0.5% to 3% of a surfactant after an immunoprecipitation reaction. In a specific embodiment of the present invention, dithiobis (succinimidyl propionate) (DSP) and dithiobismaleimido-ethane (DIME) may be used to crosslink FAK protein and bound proteins, and then washing is strongly performed to remove nonspecifically bound proteins. Furthermore, it was confirmed that 90% or more of the nonspecifically bound proteins may be efficiently removed by washing with PBS containing 1% TWEEN 20 as the surfactant, e.g., five times, as compared with performing washing with PBS containing no surfactant several times. As described, washing conditions may be optimized to perform more precise screening.

The screening method of the present invention may further include the step of identifying the proteins specifically binding to FAK, which are collected in the first step, by performing electrophoresis, Western blotting, or both after the first step.

In the screening method of the present invention, the second step may be performed using an and a linear trap quadrupole ion trap-mass spectrometer orbitrap mass spectrometer connected to a nano- and capillary-liquid chromatography column equipped with a C18 trap nanocolumn, but is not limited thereto.

In detail, a Nano-ESI(nEASY)-LTQ-Orbitrap Velos Pro is used to pass the proteins through a C18 trap column having a diameter of 75 μm and a length of 2 cm and a C18 analytical column having a diameter of 75 μm and a length of 50 cm connected thereto at a flow rate of 300 nL/min with a solvent gradient of 0.1% formic acid aqueous solution and 0.1% formic acid in acetonitrile as solvents, and subsequently, high-resolution mass spectrometry is performed using an orbitrap mass spectrometer and a linear trap quadrupole ion trap mass spectrometer, and thereby the proteins are isolated and identified. After the mass spectrometry, variables of an exclusion time of 180 seconds, a repeat count of 2, a repeat duration of 30 seconds, an exclusion mass width of 10 ppm, and an exclusion size of 500 are used, and singly charged ions are excluded from collection.

In the screening method of the present invention, the third step may be performed using a Mascow or Sequest program, but is not limited thereto. The Mascow program and Sequest program currently used in the art may be used, but the method is not limited to a particular program, as long as the above objects may be achieved. In a specific embodiment of the present invention, the third step was performed using a Mascow v.2.4 program, but is not limited thereto. In this regard, the third step may be performed under conditions where a precursor ion mass tolerance of 50 ppm, a fragment ion mass tolerance of 0.8 Da, and maximum missed cleavages of 2 are allowed, but specific operating conditions are not limited thereto.

The screening method of the present invention may further include a fourth step of analyzing signaling pathways of the proteins identified in the third step using an in silico program. Through the fourth step, intracellular sites and functions of the screened proteins and interactions of the proteins with other proteins are analyzed to predict a mechanism of action, thereby confirming their mechanism of action in the treatment of colon cancer.

Therapeutic target candidates for colon cancer which specifically bind to FAK and are screened reproducibly three times or more by the screening method of the present invention may include ABL1, ABL2, ACTB, ACTN4, ARHGEF10L, B4GN3, CADH6, CATL2, CC125, CC160, CCDC146, CDK13, CDKL3, CLSPN, COGA1, CXD4, CYS1, DESP, DJB11, DMBT1, DSP, DYH9, ELAVL1, ELAVL4, EPB41L4A, FLN, GFAP, GRB14, GSK3A, GTPB1, HORN, HSP7C, ILK, INT12, IQGA2, KLHL8, KLK6, KRIT1, LACRT, LATS1, LIRB4, LMOD3, LRRC4, MA7D2, MP2K3, MP2K4, MYH7B, MYO3G, MYO5A, MYO1D, NMDE1, NOC4L, PI4KA, PI4KB, PLK1, PLXA1, PLXA2, PPP1R12B, PTN, RB22A, RCC1, RHG01, RHG07, RHG28, RHOU, RPC1, SACS, SHPRH, SMAD6, SPTN5, SRCN1, STA13, STAR9, SYNE1, SYNE3, TJP1, TJP3, TGFI1, VGFR1, YK022, ZN408, ZN503, ZXDC, and ZYX, but are not limited thereto.

Among these, the therapeutic target candidates for colon cancer may specifically include 18 kinds of proteins such as ABL1, ELAVL1, GRB14, GSK2A, HORN, LATS1, LRRC4, MA7D2, MP2K3, MP2K4, PI4KA, PI4KB, PLK1, SHPRHX, SYNE1, SYNE3, VGFR1, and ZYX, which are associated with cancers, more frequently expressed in cancer cells than in normal intestinal epidermal cells, and involved in the FAK signaling pathways, but are not limited thereto.

The therapeutic target candidates for colon cancer may more specifically include ABL1, ELAVL1, GRB14, GSK2A, HORN, LATS1, LRRC4, MA7D2, MP2K3, MP2K4, PI4KA, PI4KB, PLK1, SHPRHX, SYNE1, SYNE3, VGFR1, and ZYX, and much more specifically, ELAVL1, SYNE1, SYNE3, and ZYX, but are not limited thereto.

A second aspect of the present invention provides a method of screening for a colon cancer-targeting therapeutic agent, the method including a first step of treating a cell lysate of a colon cancer cell line or a cell separated from a colon cancer patient with colon cancer therapeutic agent candidates; and a second step of selecting, from the colon cancer therapeutic agent candidates, inhibitors capable of inhibiting expression of an FAK-binding protein or binding between the FAK-binding protein and the FAK protein, the FAK-binding protein selected from the group consisting of ABL1, ELAVL1, GRB14, GSK2A, HORN, LATS1, LRRC4, MA7D2, MP2K3, MP2K4, PI4KA, PI4KB, PLK1, SHPRHX, SYNE1, SYNE3, VGFR1, and ZYX involved in the FAK signaling pathways, which are selected by the screening method of the first aspect with respect to FAK, which is a known protein overexpressed in cells separated from a colon cancer patient, as compared with normal intestinal epidermal cells.

As described above, FAK is overexpressed in a colon cancer patient, and thus, a substance capable of selectively inhibiting expression thereof or activity thereof is applicable as a colon cancer therapeutic agent. In particular, the 12 kinds of the proteins among the proteins screened by the first aspect of the present invention are associated with the FAK signaling pathways, and therefore, substances applicable to colon cancer treatment may be selected by screening substances capable of inhibiting binding of FAK and the proteins or expression of the proteins from colon cancer therapeutic agent candidates.

The colon cancer therapeutic agent candidates may be a series of compounds, siRNAs, other nucleic acids, proteins, polypeptides, or aptamers, but are not limited thereto.

A third aspect of the present invention provides a kit for diagnosing prognosis of colon cancer treatment, the kit including an agent capable of determining expression levels of one or more FAK-binding proteins selected from the group consisting of ABL1, ELAVL1, GRB14, GSK2A, HORN, LATS1, LRRC4, MA7D2, MP2K3, MP2K4, PI4KA, PI4KB, PLK1, SHPRHX, SYNE1, SYNE3, VGFR1, and ZYX involved in the FAK signaling pathways, the FAK-binding proteins selected by the screening method of the first aspect with respect to FAK, which is a known protein overexpressed in cells separated from a colon cancer patient, as compared with normal intestinal epidermal cells.

Specifically, the kit for diagnosing prognosis of colon cancer treatment of the present invention may include an agent capable of determining expression levels of one or more FAK-binding proteins selected from the group consisting of ELAVL1, SYNE1, SYNE3, and ZYX, but is not limited thereto.

As used herein, the term "prognosis" refers to predicting progression of a disease and death or survival outcome. More specifically, since progression of a disease may vary depending on physiological or environmental conditions of a patient, prognosis or prognosis prediction may be interpreted to mean all actions that predict the progression of the disease before/after treatment, taking into account the conditions of the patient. With respect to the objects of the present invention, the prognosis may be interpreted as actions that predict a disease-free survival rate or a survival rate of a colon cancer patient by predicting the disease progression before/after treatment of colon cancer and complete discovery. For example, predicting a "good prognosis" represents a high disease-free survival rate or a high survival rate of a colon cancer patient, whether treated or not, indicating that the colon cancer patient is more likely to be treated, and predicting a "poor prognosis" represents a low disease-free survival rate or a low survival rate of a patient after colon cancer treatment, indicating that the colon cancer patient is more likely to have a cancer recurrence or to die from colon cancer.

As used herein, the term "disease-free survival rate" means the probability of survival of a patient without cancer recurrence, whether treated or not.

As used herein, the term "survival rate" means the probability of survival of a patient regardless of cancer recurrence, whether treated or not.

As used herein, the term "diagnosis" means detection of a pathological state or condition. With respect to the objects of the present invention, the diagnosis aims to confirm metastasis or a likelihood of metastasis of colon cancer.

For example the kit may be an RT-PCR (reverse transcription polymerase chain reaction) kit, a DNA chip kit, an ELISA (enzyme linked immunosorbent assay) kit, a protein chip kit, a rapid kit, or an MRM (multiple reaction monitoring) kit, but is not limited thereto.

The kit of the present invention may be a kit including essential elements needed to perform RT-PCR. Such an RT-PCR kit may include, in addition to primers each specific to genes encoding the proteins, a test tube or other proper containers, a reaction buffer solution (pH and magnesium concentration are varied), deoxynucleotides (dNTPs), enzymes such as a Taq-polymerase and a reverse transcriptase, DNase, an RNase inhibitor, DEPC-water, sterilized water, etc. In addition, the kit may include a pair of primers each specific to a gene used as a qualitative control group.

Further, the kit of the present invention may include essential elements needed to perform a DNA chip assay. The kit for the DNA chip assay may include a substrate to which cDNA corresponding to a gene or a fragment thereof is attached as a probe, and a reagent, an agent, an enzyme, etc. to prepare a fluorescent probe. Further, the substrate may include cDNA corresponding to a quantitative control gene or a fragment thereof.

In addition, the kit of the present invention may be a kit for a protein chip assay to measure expression levels of the proteins. The kit may include, but is not particularly limited to, a substrate, an appropriate buffer, a secondary antibody labeled with a chromogenic enzyme or a fluorescent substance, or a chromogenic substrate for immunological detection of antibodies. The substrate may be, but is not particularly limited to, a nitrocellulose membrane, a 96-well plate synthesized from a polyvinyl resin, a 96-well plate synthesized from a polystyrene resin, or a glass slide. The chromogenic enzyme may be, but is not particularly limited to, peroxidase or alkaline phosphatase. The fluorescent substance may be, but is not particularly limited to, FITC or RITC. The chromogenic substrate may be, but is not particularly limited to, ABTS (2,2'-azino-bis(3-ethylbenzothiazoline-6-sulfonic acid), OPD (o-phenylenediamine), or TMB (tetramethyl benzidine).

Hereinafter, the present invention will be described in more detail with reference to Examples. However, these Examples are for illustrative purposes only, and the scope of the present invention is not intended to be limited by these Examples.

Materials

Pierce™ protein A/G agarose was purchased from Thermo Fischer Scientific. RPMI-1640 medium, fetal bovine serum (FBS), 0.25% trypsin-ethylenediaminetetraacetic acid (EDTA), and penicillin-streptomycin were purchased from Life Technologies (Carlsbad, Calif., USA). Focal adhesion kinase (FAK) antibody was purchased from Cell Signaling Technology (Beverly, Mass., USA) and secondary goat anti-rabbit IgG-HRP antibody was purchased from Santa Cruz Bio-technology Inc. (Santa Cruz, Calif., USA). Anti-beta actin (N-terminal) antibody was purchased from Younginfrontier Co. LTD. (Seoul, Korea). Human epidermal growth factor (hEGF), human insulin-like growth factor-1 (hIGF-1), phorbol 12-myristate 13-acetate (PMA), and human platelet-derived growth factor (PDGF) were purchased from Sigma-Aldrich (St. Louis, Mo., USA). Ammonium bicarbonate, DL-dithiothreitol, iodoacetamide, and trypsin needed for trypsin digestion were purchased from Sigma-Aldrich. Distilled water was double-distilled water prepared using a milli-Q water purification system (Millipore Corp., Bedford, Mass., USA).

Preparation Example 1: Cell Line and Cell Culture

A human colon cancer cell line, HCT-116, was cultured using an RPMI-1640 medium containing 10% (v/v) heat-inactivated FBS and 1% (v/v) penicillin/streptomycin in a 60 mm plastic culture plate (Corning Life Science, Acton, Mass., USA) until its cell density reached $2 \times 10^6$ cells/cm$^2$. The culture was performed in a humidified incubator of 5% $CO_2$ at 37° C. The cells were starved for 24 hours and washed with serum-free medium. FGF signaling was amplified by adding 10 ng/mL of EGF, IGF, PMA, and PDGF, followed by further incubation for 2 hours. Thereafter, the cells were harvested and collected by centrifugation at a speed of 300 g for 5 minutes. Cell membranes were disrupted using a sonicator, and centrifuged at a speed of 13,000 g for 30 minutes to collect lysed intracellular proteins. Further, to compare the amounts of expressed FAK-binding proteins by using defactinib (VS-6063) and PF-573228, which are FAK inhibitors, independently or simultaneously, normal intestinal epidermal cells and colon cancer cells were each treated with FAK inhibitors at three different final concentrations of 0.1 mM, 1 mM, and 10 mM (2 hours), and then cells were collected and subjected to in-solution digestion to isolate and identify the proteins. Furthermore, expression level ratios of the same proteins were calculated and shown in FIG. 14.

Figure 2:
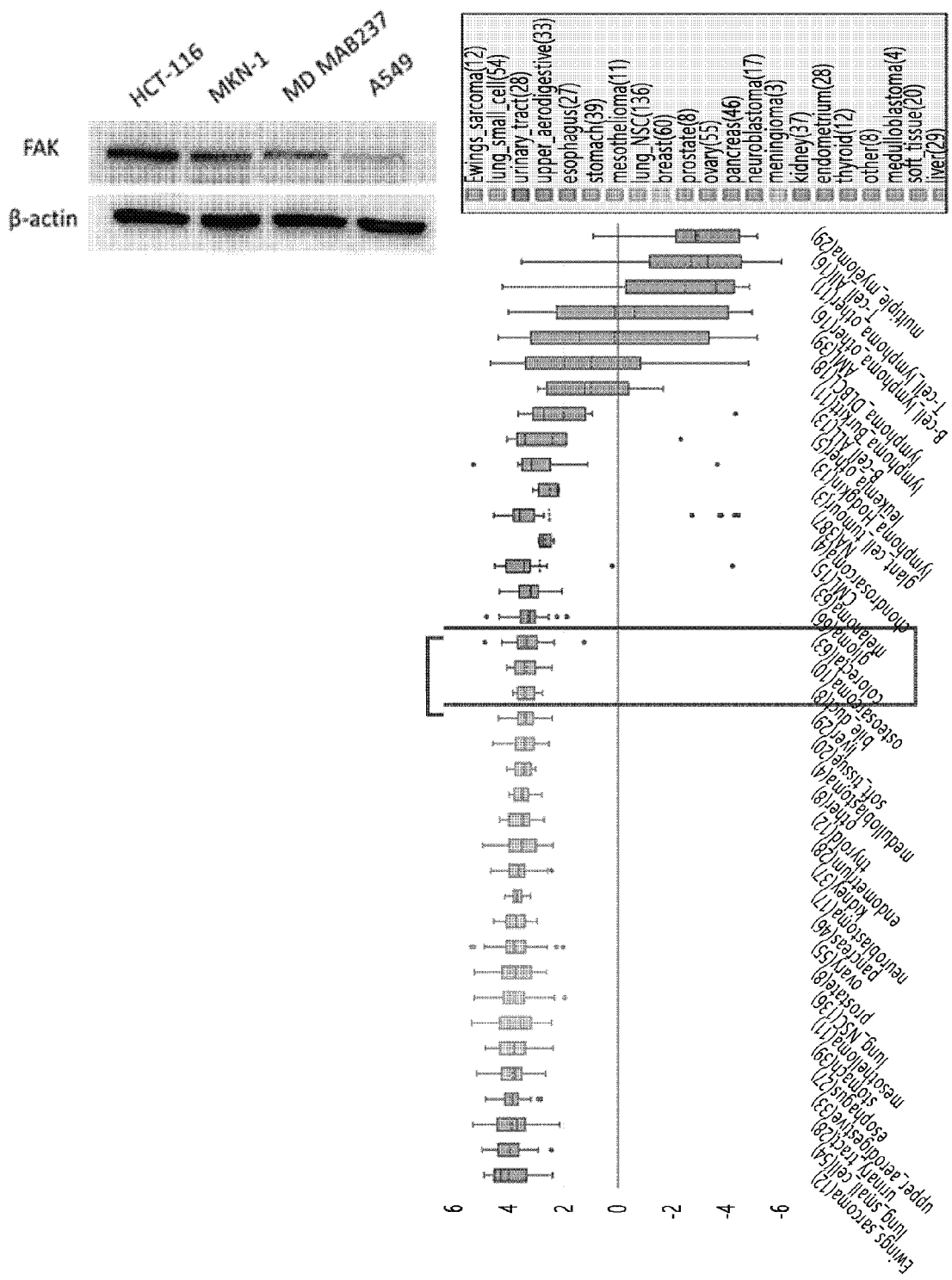
FIG. 2 shows the results of comparing and analyzing expression levels of FAK protein in colon cancer (HCT-116), stomach cancer (MKN-1), breast cancer (MD MAB237), and lung cancer (A549) cells, wherein the figure on the left shows the most remarkable expression of FAK protein in the colon cancer cell line among the four kinds of cancer cell lines, and the figure on the right shows the results of comparing mRNA levels of FAK registered in the database using IPA (Ingenuity Pathway Analysis), which is an in silico program, and remarkably high expression of mRNA in the colon cancer patient as well as in lung cancer, prostate cancer, and renal cancer patients, as compared with that of a normal person.

Example 1: Selection of Target Protein for Development of Colon Cancer-Specific Therapeutic Agents and Optimization of Reaction Conditions First, to examine whether FAK is suitable as a target protein for the development of colon cancer-specific therapeutic agents, FAK expression levels in stomach cancer (MKN-1), breast cancer (MD MAB237), and lung cancer (A549) cell lines in addition to the colon cancer cell line were measured in the same manner as in Preparation Example 1, and the results are shown in FIG. 2. As shown in FIG. 2, among the four kinds of cancer cell lines including the colon cancer cell line, the colon cancer cell line showed the most remarkably high FAK protein expression. The right side of FIG. 2 shows the results of comparing mRNA levels of FAK registered in database by IPA (Ingenuity Pathway Analysis) which is an in silico program. The results showed that remarkably high mRNA levels were observed in colon cancer patients as well as in lung cancer, prostate cancer, and renal cancer patients, as compared with normal persons.

Subsequently, in order to maximize the effect of immunoprecipitation (IP), which is the most common procedure in the method of screening for therapeutic targets of the present invention, several reaction conditions were optimized. The detailed IP method will be described in Example 2 below.

Figure 3:
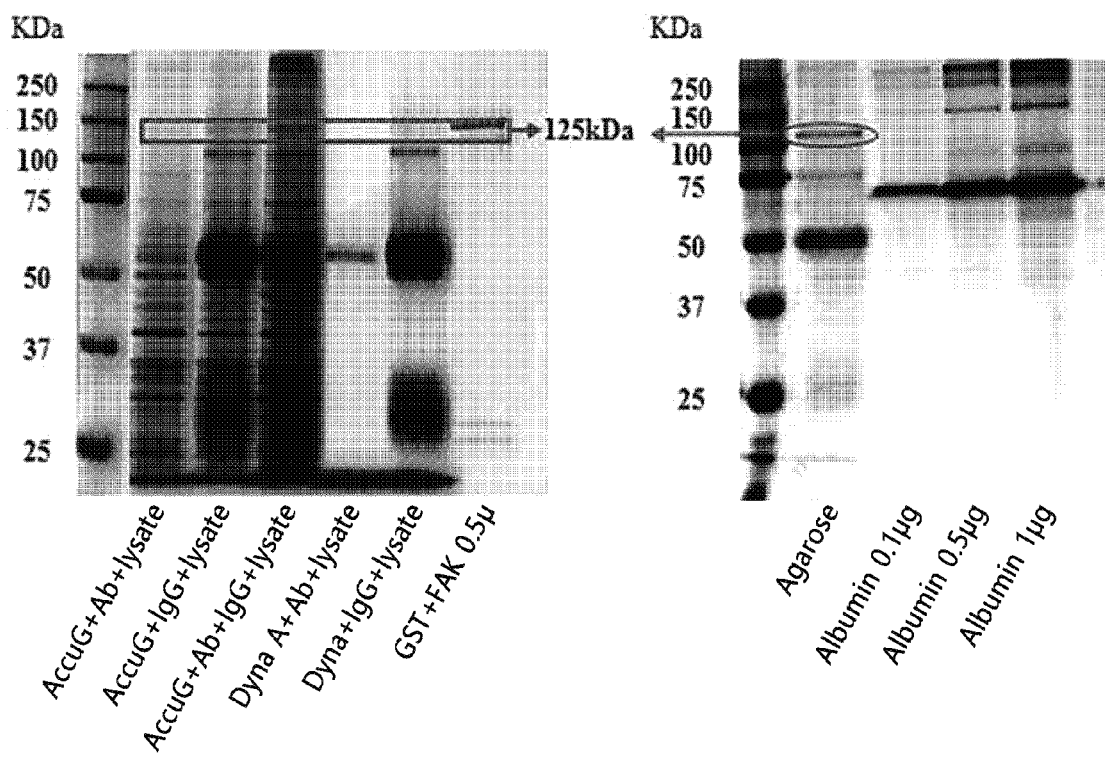
FIG. 3 shows the results of immunoprecipitation (IP) for the identification of proteins specifically binding to FAK, the immunoprecipitation performed using agarose beads and magnetic beads as immobilizers.

First, to select an IP immobilizer, agarose beads and magnetic beads were used to examine FAK adhesion, and the results are shown in FIG. 3. As shown in FIG. 3, it was confirmed that more FAK binds to agarose beads than magnetic beads, and therefore, agarose beads were used as the IP immobilizer in the subsequent experiment.

Figure 4:
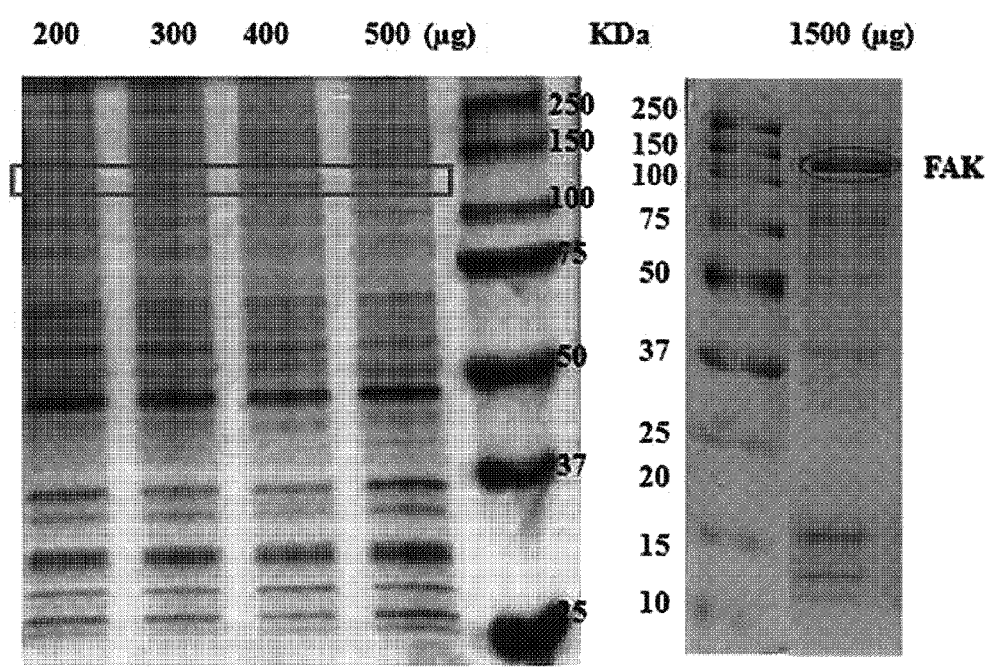
FIG. 4 shows the results of IP according to the amount of the cell lysate used.

Next, the effect according to the amount of the cell lysate used was examined. In detail, electrophoresis was performed while increasing the amount of the cell lysate from 200 μg to 1500 µg, and the results are shown in FIG. 4. As shown in FIG. 4, when 1500 µg or more of the cell lysate was used, proteins were sufficiently obtained, enabling identification of FAK-binding proteins by a Mascot search engine.

Figure 5:
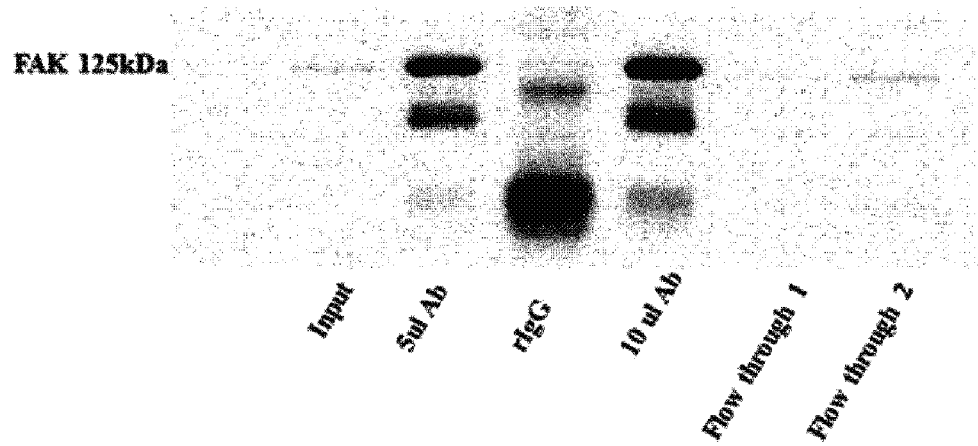
FIG. 5 shows the results of IP according to the amount of the antibody used.

Furthermore, the effect according to the amount of the antibody used was examined. The results measured while varying the amount of the antibody are shown in FIG. 5. As shown in FIG. 5, when the amount of the antibody was increased from 5 µg to 10 µg, remarkably higher amounts of FAK were recovered, and the amount of FAK which did not bind to the antibody to remain in the cell lysate was small.

Figure 6:
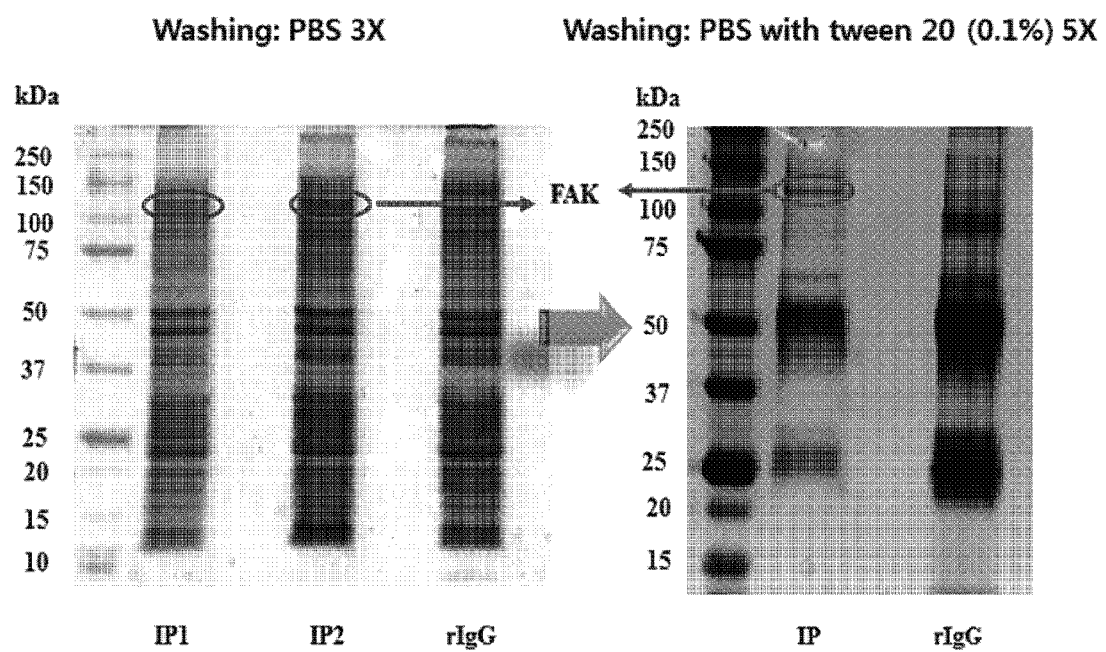
FIG. 6 shows the results of IP according to the washing method to remove nonspecifically bound proteins.

For more accurate analysis, a test was performed while varying the composition of the washing solution and the washing frequency to find a washing method capable of efficiently removing nonspecifically bound proteins after crosslinking the FAK protein and the proteins bound thereto, and the results are shown in FIG. 6. As shown in FIG. 6, when washing was performed five times using PBS containing 0.1% Tween 20 as a surfactant, bound FAK protein was observed with the naked eye only by silver staining, as compared with washing performed using PBS three times. Clear results were obtained by removing 90% of the non-specifically bound proteins.

Figure 7:
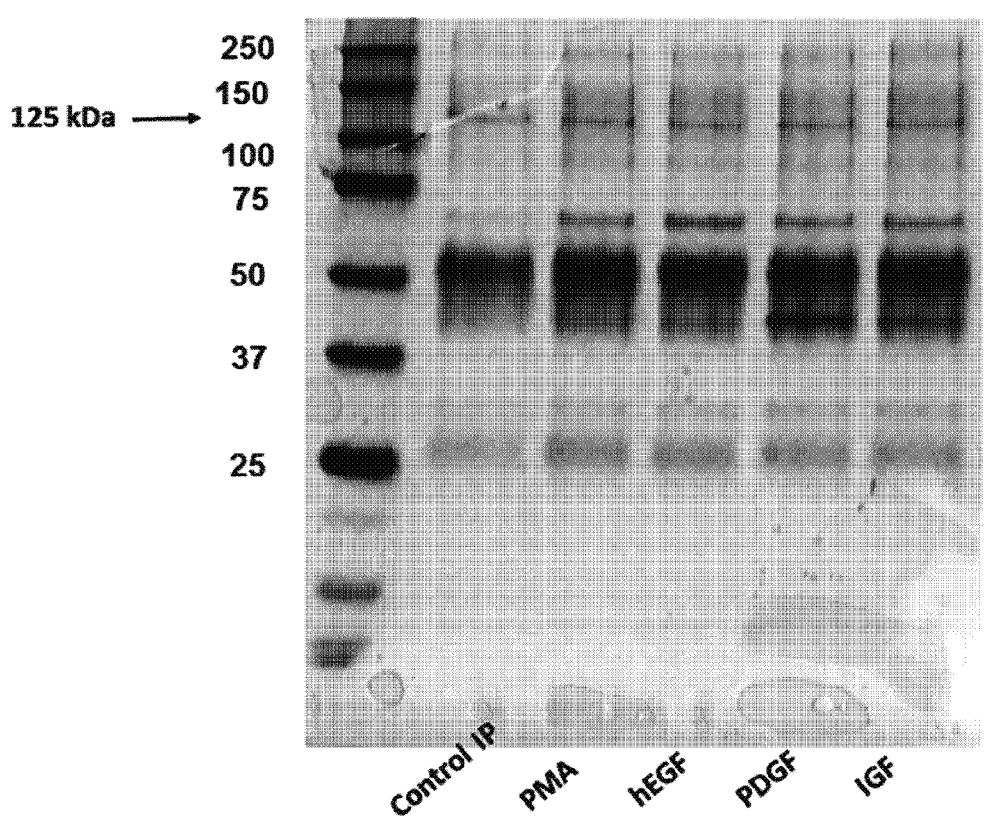
FIG. 7 shows the results of Western blotting to examine increase of the FAK-binding proteins in a colon cancer cell line HCT-116 treated with phorbol 12-myristate 13-acetate (PMA), human epidermal growth factor (hEGF), human platelet-derived growth factor (PDGF), and human insulin-like growth factor-1 (hIGF-1) which are FAK signaling substances.

Lastly, when the known FAK signaling substances were treated, complexes of the FAK protein and the proteins specifically bound thereto were increased, and the results are shown in FIG. 7. As shown in FIG. 7, it was confirmed that when FAK signaling substances, PMA, hEGF, PDGF, and IGF were treated, complexes of the FAK protein and the proteins specifically bound thereto were increased two-fold or more, as compared with a control group which was not treated with the signaling substances.

Example 2: Western Blotting and Immunoprecipitation Method

The concentrations of the collected proteins were determined using a bicinchoninic acid (BCA) protein assay kit (Thermo Fisher Scientific, Waltham, Mass., USA), and the remaining samples were separated by 10% SDS-PAGE (sodium dodecyl sulfate-polyacrylamide gel electrophoresis), and transferred to a nitrocellulose membrane (Pall Corporation, Pensacola, Fla., USA) to perform Western blotting. The membrane was blocked with PBS containing 0.2% TWEEN 20 and 5% non-fat dry milk for about 2 hours, and blotting was performed using anti-phospho-FAK (1:1000) antibody and anti-β-actin (1:5000) antibody overnight. HRP-conjugated goat anti-rabbit IgG diluted 1:5000 was used as a secondary antibody, and fluorescence images were scanned using an Ez-capture MG (ATTO, NY, USA) instrument. For IP, 1.5 mg of the cell lysate was prepared and incubated overnight with 20 µL of agarose beads preblocked (at 4° C. for 2 hours) with PBS containing 1% bovine serum albumin (BSA), wherein 10 µL of FAK antibody (1:500) was immobilized to the agarose beads. To remove nonspecific binding, the beads were washed with 600 µL of PBS containing 0.1% TWEEN 20 twice, and FAK protein and proteins bound thereto were crosslinked using 2 mM of dithiobis(succinimidyl propionate) (DSP) and dithiobismaleimidoethane (DTME). The crosslinking agents were dissolved in 20 mM DMSO and diluted with PBS (pH 7.4), and then used in the reaction. Washing was performed five times using 600 µL of a 0.1% solution of PBS-Tween 20 and further performed using PBS twice. Then, the sample was dissolved in 40 µL of 2× Laemmli sample buffer (LSB) and boiled at 95° C. for 10 minutes to separate the proteins from the beads. Rabbit IgG (1 µg/µL, 10 µL) used as a negative control was also subjected to IP in the same manner as above.

Example 3: SDS-PAGE and In-Gel Digestion

The samples obtained in Example 2 were loaded on a 10% bis-tri gel to perform electrophoresis. Running was performed using a MOPS SDS running buffer at 100 V for about 1 hour and 30 minutes. The electrophoresed gel was stained using a silver kit (ATTO), and bands that appeared were cut in a size of 1 mm to 2 mm and subjected to reduction (1 mM DTT, 60° C., 1 hour) and alkylation (55 mM iodoacetamide, at room temperature in the dark). After dehydration with 100% acetonitrile, the gel was dissolved in 15 ng/mL of trypsin (Pierce) solution and 100 µL of 50 mM ammonium bicarbonate buffer, and treated with trypsin at a ratio of 1:30 (trypsin:protein, w/w) and stored at 37° C. for 24 hours. After 24 hours, peptides were extracted with a 1:2 (v/v) mixture of 5% formic acid/acetonitrile, and concentrated by centrifugation under reduced pressure, and salts were removed therefrom using a C18 spin column (Pierce).

Example 4: Analysis by Nano-Liquid Chromatography/High-Resolution Mass Spectrometry The samples obtained in Example 3 were analyzed using an EASY-nLC1000 liquid chromatography system-connected LTQ Orbitrap Velos Pro mass spectrometer (Thermo Fischer Scientific, Sunnyvale, Calif., USA). As solvents, 0.1% formic acid in DI water (solvent A) and 0.1% formic acid in acetonitrile (solvent B) were prepared. In the liquid chromatography system, a column constituted by connecting a 2 cm C18 trap nanocolumn (Acclaim PepMap 100, 75 µL, Thermo Scientific) to a 50 cm EASY-Spray column (PepMap, 75 µL, Thermo Scientific) was used. Solvents A and B prepared as above were mixed, and the mixture was applied at a flow rate of 300 nL/min for 120 minutes with a 5% to 40% gradient to solvent B. A spray voltage of 1.8 kV was applied in a positive ion mode, and data-dependent MS/MS spectra were collected. A collision-induced dissociation (CID) energy was 35 V, and variables of an exclusion time of 180 seconds, a repeat count of 2, a repeat duration of 30 seconds, an exclusion mass width of 10 ppm, and an exclusion size of 500 were used. Singly charged ions were excluded from collection.

Figure 8:
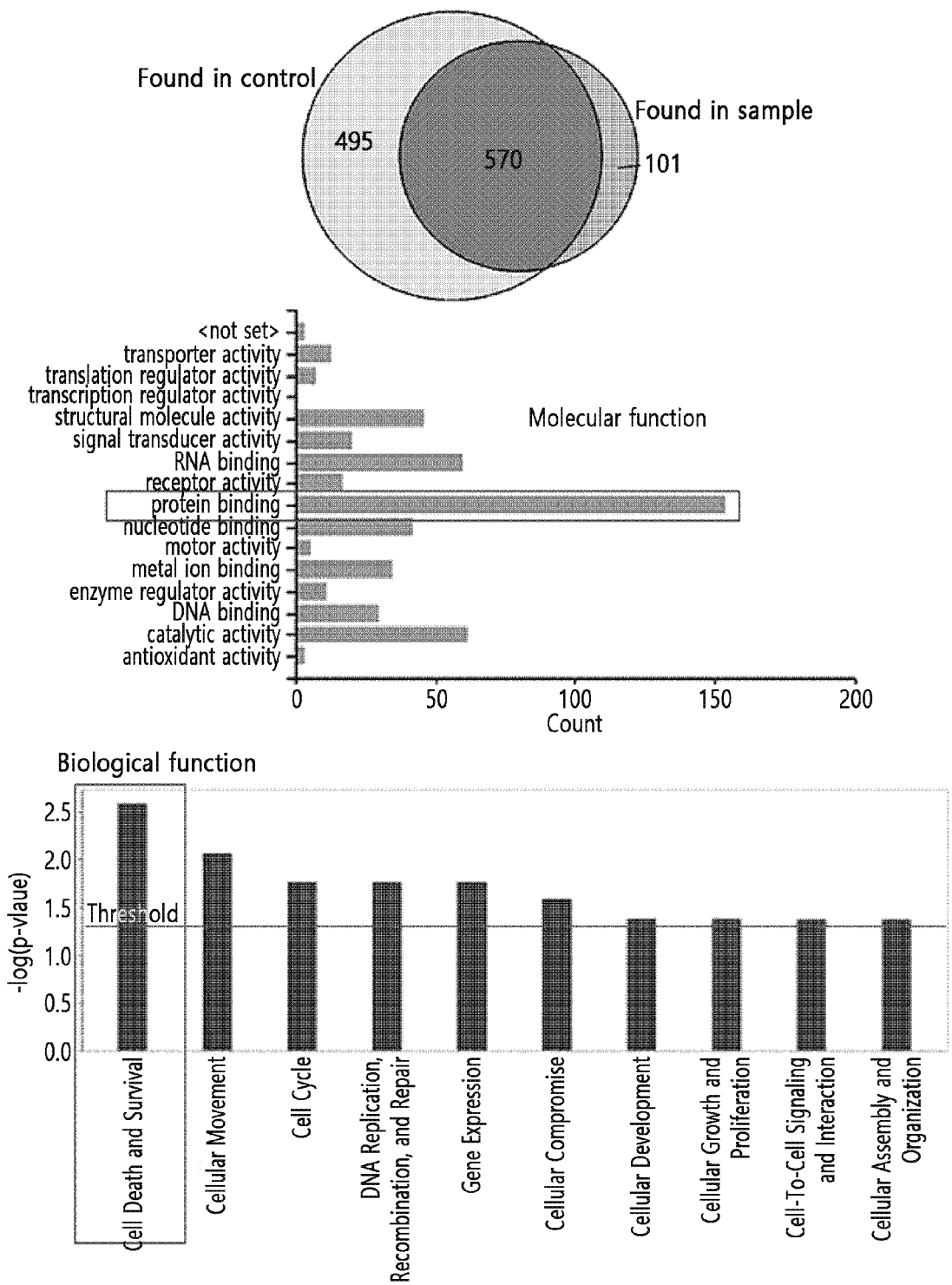
FIG. 8 shows molecular or biological functions of FAK-binding proteins, together with frequency, wherein after hEGF treatment, the FAK-binding proteins were separated by SDS-PAGE, digested with trypsin, and analyzed and identified by nano-liquid chromatography/high-resolution mass spectrometry.
Figure 12:
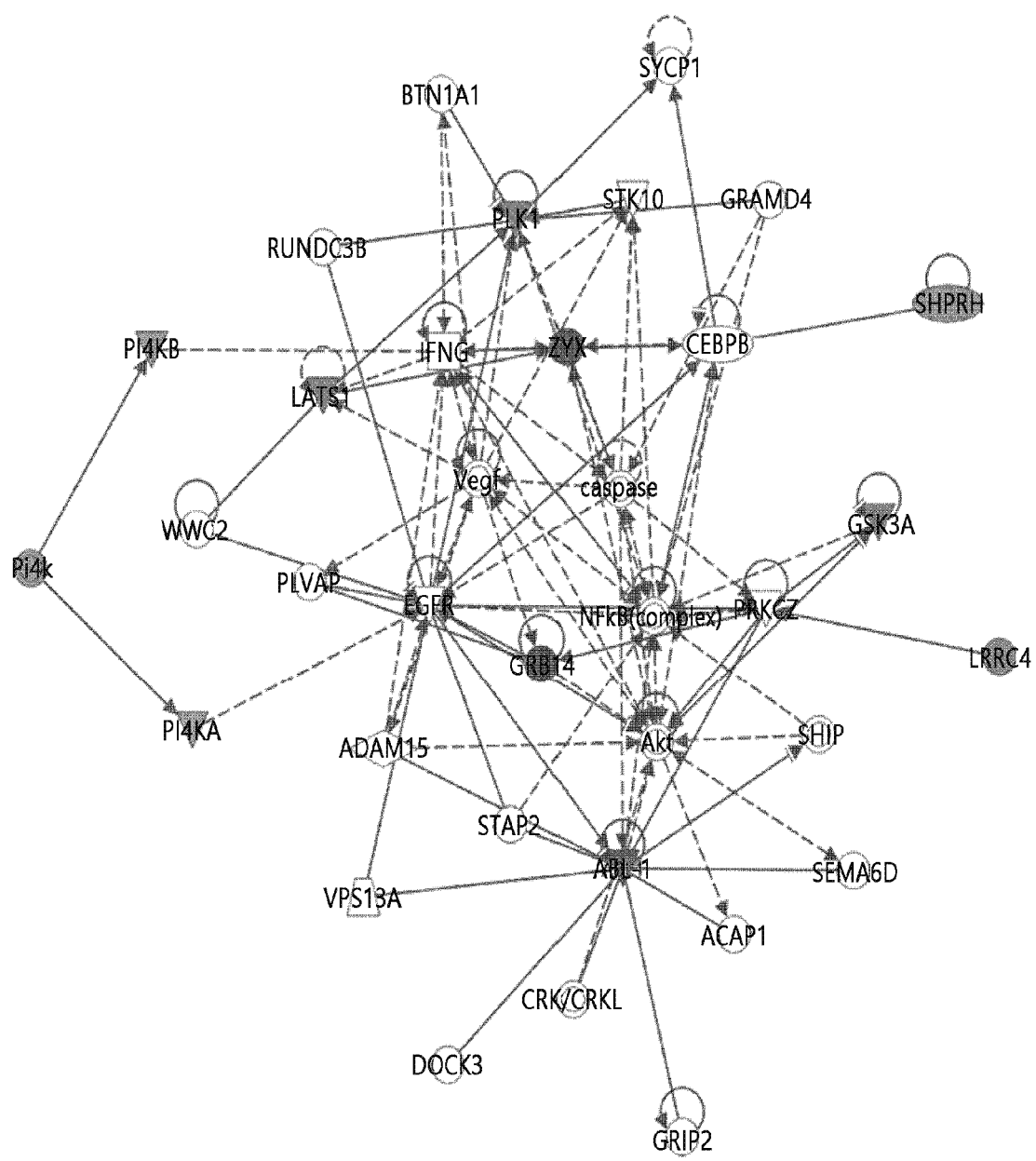
FIG. 12 shows interactions between FAK-binding proteins identified in the FAK signaling pathway and other proteins.

With regard to cells treated with an FAK signaling substance hEGF, molecular or biological functions associated with the proteins which were analyzed and identified by nano-liquid chromatography/high-resolution mass spectrometry of the samples obtained in Examples 2 and 3 are shown, with frequency, in FIG. 8. As shown in FIG. 8, with regard to molecular functions, proteins involved in the protein binding were predominant, and with regard to biological functions, proteins involved in the cell death and survival were the most predominant, followed by proteins involved in cellular movement and cell cycle.

Example 5: Peptide Sequence Analysis Using Mascot and Statistical Analysis

From the peaks detected by nano-liquid chromatography/high-resolution mass spectrometry in Example 4, proteins were identified using the Mascot v.2.4 (Matrix science Inc., Boston, Mass., USA) program, wherein a precursor ion mass tolerance of 50 ppm, a fragment ion mass tolerance of 0.8

Da, and maximum missed cleavages of 2 were allowed, and oxidation was set as a variable modification. A chi-squared test was used for statistical analysis between different groups.

From the proteins specifically binding to the FAK protein isolated from colon cancer cell samples, which were obtained by analyzing the above IP results using the Mascot search engine, 84 kinds of proteins detected reproducibly three times or more were identified, and the results are shown alphabetically in FIG. 9. As shown in FIG. 9, integrin-linked protein kinase (ILK) and SRC kinase, which are known to bind to FAK, were detected together with FAK.

Further, a total of 18 kinds of binding proteins which are associated with cancer and expressed with higher frequency in cancer cells than in normal intestinal epidermal cells, obtained through a literature search, are shown in FIG. 10. A non-patent literature document reported high expression of GRB14 (growth factor receptor-bound protein 14), MA7D2 (MAP7 domain-containing protein 2), and PLK1 (Serine/threonine-protein kinase) in colon cancer.

Meanwhile, FIG. 11 shows information on the in silico gene pathway of 12 kinds of the proteins having networks with the FAK signaling pathway, among the 18 kinds of the FAK-binding proteins shown in FIG. 10. As shown in FIG. 11A, statistical analysis of the intracellular expression sites showed that ABL1, GSK3A, LATS1, PLK1, SHPRHb, SYNE1, and SYNE3, occupying about 58%, were located in the nucleus, GRB14, LRRC4, and ZYX, occupying 25%, were located in the plasma membrane, and PI4KA and PI4KB, occupying 17%, were present in the cytoplasm. As shown in FIG. 11B, in which 12 kinds of the new drug target candidates were categorized into protein types, 50% of the proteins were kinases, 8% were transcription regulators, and 42% were other proteins.

FIGS. 13A to 13D show lists of proteins of which expression was increased 10-fold or more in a colon cancer cell line HCT-116 treated with hEGF, hIGF-1, PDGF, and PMA, which are known to increase FAK signaling, as compared with cells not treated with the FAK signaling substance, wherein the FAK-binding proteins were obtained by analysis of nano-liquid chromatography/high-resolution mass spectrometry after in-gel digestion of Western blotting results and by identifying using the Mascot search engine. As a result, SYNE1, TJP3, ELAVL4, ARHGEF10L, and DSP were detected reproducibly.

FIG. 14 shows protein candidates showing significant changes in the expression levels, among proteins of colon cancer cells, when they were treated with the known FAK inhibitors, VS-6063 and PF-573228, singly or in combination. ZYX, ELAVL1, SYNE1, MAP2K2, PPP2, and ARFGEF showed statistically significant reduction in the expression levels due to treatment of the FAK inhibitors. Specifically, ZYX, ELAVL1, and SYNE1 showed changes in the expression levels due to both of the two inhibitors. MAP2K2 and PPP2 showed changes in the expression levels only with the selective FAK inhibitor VS-6063, whereas ARFGEF showed a significant reduction in the expression level only with the ATP competitive inhibitor PF-573228. Among these, FAK-binding proteins confirmed by immunoprecipitation were ZYX, ELAVL1, SYNE1, MAP2K2, and ARFGEF.

EFFECT OF THE INVENTION

A screening method of the present invention, which is performed by a series of processes consisting of immunoprecipitation, analysis through liquid chromatography-mass spectrometry, and protein identification using a proteomics database search engine, may include a series of processes including specific selection, isolation, and identification of proteins, thereby enabling screening of therapeutic targets through a multi-step verification process. Therefore, therapeutic target candidates screened thereby may be usefully applied to the development of colon cancer therapeutic agents. Furthermore, these proteins may also be used in a kit for diagnosing treatment prognosis of colon cancer patients.

What is claimed is:

1. A method of screening for therapeutic targets to develop therapeutic agents for colon cancer, the method comprising:
   a first step of collecting proteins specifically binding to focal adhesion kinase (FAK), which is overexpressed in cells separated from a colon cancer patient, as compared with normal intestinal epidermal cells, by immunoprecipitation (IP) of a cell lysate of a colon cancer cell line or a cell separated from a colon cancer patient with an antibody against FAK, which is overexpressed in cells separated from a colon cancer patient, as compared with normal intestinal epidermal cells;
   a second step of isolating and analyzing the proteins obtained from the first step by liquid chromatography-mass spectrometry; and
   a third step of identifying the proteins isolated and analyzed by the second step using a proteomics database search engine.

2. The method of claim 1, wherein the cell lysate is a lysate of a colon cancer cell line cultured in a medium containing FAK signaling substances or a cell separated from a colon cancer patient.

3. The method of claim 1, wherein the immunoprecipitation is performed using protein A/G agarose beads onto which FAK antibodies are immobilized.

4. The method of claim 1, wherein the immunoprecipitation further includes the step of removing nonspecifically bound proteins by washing with a buffer containing 0.5% to 3% of a surfactant after a immunoprecipitation reaction.

5. The method of claim 1, further comprising the step of identifying the proteins specifically binding to FAK, which are collected in the first step, by performing electrophoresis, Western blotting, or both thereof after the first step.

6. The method of claim 1, wherein the second step is performed using an orbitrap mass spectrometer and a linear trap quadrupole ion trap-mass spectrometer connected to a nano- and capillary-liquid chromatography column equipped with a C18 trap nanocolumn.

7. The method of claim 1, wherein the third step is performed using a Mascow or Sequest program.

8. The method of claim 1, further comprising a fourth step of analyzing signaling pathways using an in silico program.

9. The method of claim 1, wherein therapeutic target candidates for colon cancer which specifically bind to FAK and are screened reproducibly three times or more by the screening method are selected from the group consisting of ABL1, ABL2, ACTB, ACTN4, ARHGEF10L, B4GN3, CADH6, CATL2, CC125, CC160, CCDC146, CDK13, CDKL3, CLSPN, COGA1, CXD4, CYS1, DESP, DJB11, DMBT1, DSP, DYH9, ELAVL1, ELAVL4, EPB41L4A, FLN, GFAP, GRB14, GSK3A, GTPB1, HORN, HSP7C, ILK, INT12, IQGA2, KLHL8, KLK6, KRIT1, LACRT, LATS1, LIRB4, LMOD3, LRRC4, MA7D2, MP2K3, MP2K4, MYH7B, MYO3G, MYO5A, MYO1D, NMDE1, NOC4L, PI4KA, PI4KB, PLK1, PLXA1, PLXA2, PPP1R12B, PTN, RB22A, RCC1, RHG01, RHG07, RHG28, RHOU, RPC1, SACS, SHPRH, SMAD6, SPTN5, SRCN1, STA13, STARS, SYNE1, SYNE3, TJP1, TJP3, TGFI1, VGFR1, YK022, ZN408, ZN503, ZXDC, and ZYX.

10. A method of screening for a colon cancer-targeting therapeutic agent, the method comprising:
   a first step of treating a cell lysate of a colon cancer cell line or a cell separated from a colon cancer patient with colon cancer therapeutic agent candidates; and
   a second step of selecting, from the colon cancer therapeutic agent candidates, inhibitors capable of inhibiting expression of an FAK-binding protein or binding between the FAK-binding protein and the FAK protein, the FAK-binding protein selected from the group consisting of ABL1, ELAVL1, GRB14, GSK2A, HORN, LATS1, LRRC4, MA7D2, MP2K3, MP2K4, PI4KA, PI4KB, PLK1, SHPRHX, SYNE1, SYNE3, VGFR1, and ZYX involved in the FAK signaling pathways, which are selected by the screening method of claim 1 with respect to FAK, which is a known protein overexpressed in cells separated from a colon cancer patient, as compared with normal intestinal epidermal cells.

11. The method of claim 10, wherein the cell lysate is a lysate of a colon cancer cell line cultured in a medium containing FAK signaling substances or a cell separated from a colon cancer patient.

12. The method of claim 10, wherein the immunoprecipitation is performed using protein A/G agarose beads onto which FAK antibodies are immobilized.

13. The method of claim 10, wherein the immunoprecipitation further includes the step of removing nonspecifically bound proteins by washing with a buffer containing 0.5% to 3% of a surfactant after a immunoprecipitation reaction.

14. The method of claim 10, further comprising the step of identifying the proteins specifically binding to FAK, which are collected in the first step, by performing electrophoresis, Western blotting, or both thereof after the first step.

15. The method of claim 10, wherein the second step is performed using an orbitrap mass spectrometer and a linear trap quadrupole ion trap-mass spectrometer connected to a nano- and capillary-liquid chromatography column equipped with a C18 trap nanocolumn.

16. The method of claim 10, wherein the third step is performed using a Mascow or Sequest program.

17. The method of claim 10, further comprising a fourth step of analyzing signaling pathways using an in silico program.

18. The method of claim 10, wherein therapeutic target candidates for colon cancer which specifically bind to FAK and are screened reproducibly three times or more by the screening method are selected from the group consisting of ABL1, ABL2, ACTB, ACTN4, ARHGEF10L, B4GN3, CADH6, CATL2, CC125, CC160, CCDC146, CDK13, CDKL3, CLSPN, COGA1, CXD4, CYS1, DESP, DJB11, DMBT1, DSP, DYH9, ELAVL1, ELAVL4, EPB41L4A, FLN, GFAP, GRB14, GSK3A, GTPB1, HORN, HSP7C, ILK, INT12, IQGA2, KLHL8, KLK6, KRIT1, LACRT, LATS1, LIRB4, LMOD3, LRRC4, MA7D2, MP2K3, MP2K4, MYH7B, MYO3G, MYO5A, MYO1D, NMDE1, NOC4L, PI4KA, PI4KB, PLK1, PLXA1, PLXA2, PPP1R12B, PTN, RB22A, RCC1, RHG01, RHG07, RHG28, RHOU, RPC1, SACS, SHPRH, SMAD6, SPTN5, SRCN1, STA13, STAR9, SYNE1, SYNE3, TJP1, TJP3, TGFI1, VGFR1, YK022, ZN408, ZN503, ZXDC, and ZYX.

* * * * *